United States Patent
Harichian et al.

(10) Patent No.: US 6,852,310 B2
(45) Date of Patent: *Feb. 8, 2005

(54) SKIN LIGHTENING AGENTS, COMPOSITIONS AND METHODS

(75) Inventors: Bijan Harichian, Warren, NJ (US); Michael James Barratt, Oak Ridge, NJ (US); Carol Annette Bosko, Oradell, NJ (US)

(73) Assignee: Unilever Home & Personal Care USA division of Conopco, Inc., Greenwich, CT (US)

(*) Notice: Subject to any disclaimer, the term of this patent is extended or adjusted under 35 U.S.C. 154(b) by 252 days.

This patent is subject to a terminal disclaimer.

(21) Appl. No.: 10/227,642

(22) Filed: Aug. 23, 2002

(65) Prior Publication Data

US 2004/0042983 A1 Mar. 4, 2004

(51) Int. Cl.[7] .................. A61K 7/42; A61K 7/44; A61K 7/00
(52) U.S. Cl. .................. 424/59; 424/60; 424/400; 424/401
(58) Field of Search .................. 424/59, 60, 70.1, 424/400, 401

(56) References Cited

U.S. PATENT DOCUMENTS

| | | | |
|---|---|---|---|
| 5,766,575 | A | 6/1998 | Crotty et al. |
| 6,132,740 | A | 10/2000 | Hu |
| 6,403,065 | B1 | 6/2002 | Chevalier et al. |

FOREIGN PATENT DOCUMENTS

| | | |
|---|---|---|
| DE | 20110355 | 6/2001 |
| EP | 1 134 207 | 9/2001 |
| GB | 1 581 428 | 10/1980 |
| JP | 01-10925 | 11/2000 |
| JP | 00-327557 | 1/2001 |

WO 02/24613 3/2002

OTHER PUBLICATIONS

Lille, et al., Tr.Nauch–Issled. Inst. slantsev 1969, No. 18, pp. 127–134.
International Search Report No. PCT/EP 03/08845 dated Jan. 2, 2004—3 pp.

Primary Examiner—Shelley A. Dodson
(74) Attorney, Agent, or Firm—Ellen Plotkin

(57) ABSTRACT

Cosmetic methods of skin lightening using coumarin derivatives of formula I as skin lightening agents alone or in combination with other skin benefit agents and together with a cosmetic vehicle:

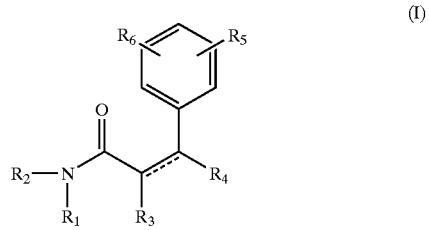

(I)

Where each or both $R_1$ and/or $R_2$ represents hydrogen; linear or branched $C_1$–$C_{18}$ alkyl, alkenyl, cycloalkyl, cycloalkenyl, hydroxyalkyl, hydroxyalkenyl, acyl, cycloacyl, or alkoxy groups;

Each or both $R_3$ and/or $R_4$, which may be connected by a single or double carbon-carbon bond (shown as a dotted line), represents hydrogen; linear or branched $C_1$–$C_{18}$ alkyl, alkenyl, alkoxy, cycloalkyl, or cycloalkenyl group; and Each or both $R_5$ and/or $R_6$ represents a hydrogen atom, OH, $C_1$–$C_4$ acyl group, $C_1$–$C_4$ alkyl group, O—CO—$R_7$, O—COO—$R_8$ group, mesyl group or tosyl group, where each or both $R_7$ and/or $R_8$ represents hydrogen; linear or branched $C_1$–$C_{18}$ alkyl, alkenyl, hydroxyalkyl, hydroxyalkenyl, acyl, cycloacyl, or alkoxy groups.

14 Claims, No Drawings

SKIN LIGHTENING AGENTS, COMPOSITIONS AND METHODS

FIELD OF THE INVENTION

The invention relates to cosmetic methods of using coumarin derived compounds and cosmetic compositions including same, and more specifically, coumarin derived resorcinol derivatives, as skin lightening agents.

BACKGROUND OF THE INVENTION

Many people are concerned with the degree of pigmentation of their skin. For example, people with age spots or freckles may wish such pigmented spots to be less pronounced. Others may wish to reduce the skin darkening caused by exposure to sunlight or to lighten their natural skin color. To meet this need, many attempts have been made to develop products that reduce the pigment production in the melanocytes. However, the substances identified thus far tend to have either low efficacy or undesirable side effects, such as, for example, toxicity or skin irritation. Therefore, there is a continuing need for new skin lightening agents, with improved overall effectiveness.

Resorcinol derivatives have cosmetic skin and hair benefits. Certain resorcinol derivatives, particularly 4-substituted resorcinol derivatives, are useful in cosmetic compositions for skin lightening benefits. Resorcinol derivatives are described in many publications, including Hu et al., U.S. Pat. No. 6,132,740 and European Patent Application EP 1 134 207; and Japanese published patent applications JP 2001-010925 and JP2000-327557. Resorcinol derivatives are known compounds and can be readily obtained by various means, including by a method wherein a saturated carboxylic acid and resorcinol are condensed in the presence of zinc chloride and the resultant condensate is reduced with zinc amalgam/hydrochloric acid (Lille, et al., Tr. Nauch-Issled. Inst. Slantsev 1969, No. 18:127–134), or by a method wherein resorcinol and a corresponding alkyl alcohol are reacted in the presence of an alumina catalyst at a high temperature of from 200 to 400° C. (British Patent No. 1,581,428). Some of these compounds can be irritating to the skin.

Applicants have now discovered that the use of compounds that which may be derived from coumarin derivatives (although not limited to such process), deliver skin lightening benefits. The general chemical formulas and structures of these compounds is discussed in more detail herein below. Hydroxy coumarin derived compounds, and especially 7-hydroxy-coumarin derived compounds which resemble resorcinol derivatives, have been found to be effective and possibly less irritating to the skin. These compounds are referred to herein as "coumarin derived resorcinol derivatives."

Aminophenol derivatives have been described as optical brighteners in, for example, Chevalier et al., U.S. Pat. No. 6,403,065. Wella AG, German Patent Application DE 20110355 relates to preparation of (dihydroxyphenyl) acrylamide derivatives and compositions containing hair coloring agents. However, coumarin derived resorcinol derivatives of the present invention have not been used for lightening skin.

SUMMARY OF THE INVENTION

The use of compounds of the general formula I, and compositions including same, delivers skin lightening benefits with potential reduced irritation. The present invention provides a cosmetic method of skin lightening using a composition comprising in addition to a cosmetically acceptable vehicle, about 0.000001 to about 50% of a compound of formula I,

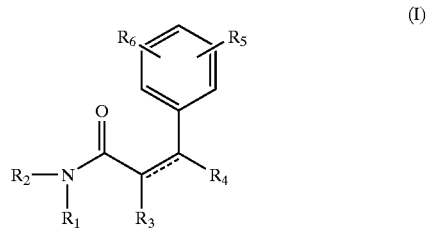

(I)

Where each or both $R_1$ and/or $R_2$ represents hydrogen; linear or branched $C_1$–$C_{18}$ alkyl, alkenyl, cycloalkyl, cycloalkenyl, hydroxyalkyl, hydroxyalkenyl, acyl, cycloacyl, or alkoxy groups. Preferably, one of $R_1$ or $R_2$ represents hydrogen and the other of $R_1$ or $R_2$ represents an alkoxy group; more preferably, the alkoxy group is $CH_2CH_2OMe$ or $CH_2CH_2CH_2OMe$; and Each or both $R_3$ and/or $R_4$ which may be connected by a single or double carbon-carbon bond (shown as a dotted line), represents hydrogen; linear or branched $C_1$–$C_{18}$ alkyl, alkenyl, alkoxy, cycloalkyl, or cycloalkenyl group. Preferably, $R_3$ and $R_4$ are connected by a double carbon-carbon bond, and both represent hydrogen; and $R_5$ and/or $R_6$ may be positioned at the 1-, 2-, 3-, 5-, and/or 6-positions on the phenyl ring. Each or both $R_5$ and/or $R_6$ represents a hydrogen atom, OH, $C_1$–$C_4$ acyl group, $C_1$–$C_4$ alkyl group, O—CO—$R_7$, O—COO—$R_8$ group, mesyl group or tosyl group, where each or both $R_7$ and/or $R_8$ represents hydrogen; linear or branched $C_1$–$C_{18}$ alkyl, alkenyl, hydroxyalkyl, hydroxyalkenyl, acyl, cycloacyl, or alkoxy groups. In a preferred embodiment, each or both $R_5$ and/or $R_6$ represents OH. In a more preferred embodiment, both $R_5$ and $R_6$ represent OH. This more preferred embodiment, referred to herein as 7-hydroxy-coumarin derivatives, or coumarin derived resorcinol derivatives, may be prepared by reaction of methylamine with 7-hydroxy-coumarin, by a method known in the art. The hydroxy groups ($R_5$ and $R_6$), as well as the $R_3$ and $R_4$ groups may be further substituted by methods known in the art.

Further skin benefit agents may be included in the compositions useful for the inventive method. Organic and inorganic sunscreens may also be included.

The inventive compositions and methods have effective skin lightening properties, may be less irritating to the skin, and are cost-effective.

DETAILED DESCRIPTION OF THE INVENTION

As used herein, the term "cosmetic composition" is intended to describe compositions for topical application to human skin.

The term "skin" as used herein includes the skin on the face, neck, chest, back, arms, axilla, hands, legs, and scalp.

Except in the examples, or where otherwise explicitly indicated, all numbers in this description indicating amounts of material or conditions of reaction, physical properties of materials and/or use are to be understood as modified by the word "about". All amounts are by weight of the composition, unless otherwise specified.

It should be noted that in specifying any range of concentration, any particular upper concentration can be associated with any particular lower concentration.

For the avoidance of doubt the word "comprising" is intended to mean including but not necessarily consisting of or composed of. In other words the listed steps or options need not be exhaustive.

Skin Lightening Agents

The invention is concerned with the use of compounds of general formula I, shown below, and compositions including same, as skin lightening agents. A particular advantage of the inventive compositions and methods is that compounds of general formula I can be less irritating to the skin than skin lightening compounds with similar structure, such as 4-substituted resorcinol derivatives:

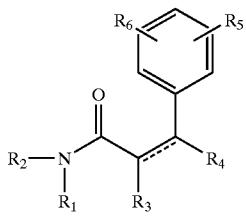
(I)

Each or both $R_1$ and/or $R_2$ represents hydrogen; linear or branched $C_1$–$C_{18}$ alkyl, alkenyl, cycloalkyl, cycloalkenyl, hydroxyalkyl, hydroxyalkenyl, acyl; cycloacyl, or alkoxy groups. Preferably, one of $R_1$ or $R_2$ represents hydrogen and the other of $R_1$ or $R_2$ represents an alkoxy group; more preferably, the alkoxy group is $CH_2CH_2OMe$ or $CH_2CH_2CH_2OMe$.

Each or both $R_3$ and/or $R_4$, which may be connected by a single or double carbon-carbon bond (shown as a dotted line), represents hydrogen; linear or branched $C_1$–$C_{18}$ alkyl, alkenyl, alkoxy, cycloalkyl, or cycloalkenyl group. Preferably, $R_3$ and $R_4$ are connected by a double carbon-carbon bond, and both represent hydrogen.

$R_5$ and/or $R_6$ may be positioned at the 1-, 2-, 3-, 5-, and/or 6-positions on the phenyl ring, and this is denoted in the structure of the compound of formula I by elongated lines generally positioned in the phenyl ring but not attached to any of these particular positions on the phenyl ring. Each or both $R_5$ and/or $R_6$ represents a hydrogen atom, OH, C1–C4 acyl group, C1–C4 alkyl group, O—CO—$R_7$ O—COO—$R_8$ group, mesyl group or tosyl group, where each or both $R_7$ and/or $R_8$ represents hydrogen; linear or branched $C_1$–$C_{18}$ alkyl or alkenyl; hydroxyalkyl; hydroxyalkenyl; acyl; cycloacyl; or alkoxy groups. In a preferred embodiment, each or both $R_5$ and/or $R_6$ represents OH. In a more preferred embodiment, both $R_5$ and $R_6$ represent OH.

In a most preferred embodiment, both $R_5$ and $R_6$ represent OH and are at the 1- and 3-positions, shown as compound of formula II, where $R_3$ and $R_4$ are both hydrogen and are connected by a double carbon-carbon bond. This most preferred embodiment, referred to herein as 7-hydroxy-coumarin derivatives, or coumarin derived resorcinol derivatives, may be prepared by reaction of methylamine ($MeNH_2$) with 7-hydroxy-coumarin, by a method known in the art. Other methods of deriving compound of formula II may also be available and the invention is not limited by the method of preparation. The hydroxy groups ($R_5$ and $R_6$), as well as the $R_1$ and $R_2$ groups may be further substituted by methods known in the art, to arrive at variations of this compound, as described generally with reference to compounds of formula I.

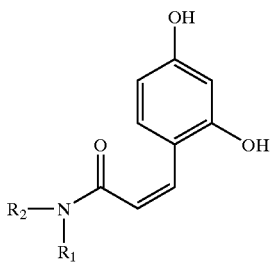
(II)

The compositions generally contain about 0.000001 to about 50% of coumarin derived compounds of general formula I. Compounds of formula II are preferred. The amount of the coumarin derivative is preferably in the range of about 0.00001% to about 10%, more preferably about 0.001 to about 7%, most preferably from 0.01 to about 5%, of the total amount of a cosmetic composition.

Optional Skin Benefit Agents

Preferred cosmetic compositions are those suitable for the application to human skin according to the method of the present invention, which optionally, but preferably, include a skin benefit agent in addition to a coumarin derivative.

Suitable additional skin benefit agents include anti-aging, wrinkle-reducing, skin whitening, anti-acne, and sebum reduction agents. Examples of these include alpha-hydroxy acids, beta-hydroxy acids, polyhydroxy acids, hydroquinone, t-butyl hydroquinone, Vitamic C derivatives, dioic acids, retinoids, and resorcinol derivatives.

Cosmetically Acceptable Carrier

The cosmetically acceptable vehicle may act as a dilutant, dispersant or carrier for the skin benefit ingredients in the composition, so as to facilitate their distribution when the composition is applied to the skin.

The vehicle may be aqueous, anhydrous or an emulsion. Preferably, the compositions are aqueous or an emulsion, especially water-in-oil or oil-in-water emulsion, preferentially oil in water emulsion. Water when present will be in amounts which may range from 5 to 99%, preferably from 20 to 70%, optimally between 40 and 70% by weight.

Besides water, relatively volatile solvents may also serve as carriers within compositions of the present invention. Most preferred are monohydric $C_1$–$C_3$ alkanols. These include ethyl alcohol, methyl alcohol and isopropyl alcohol. The amount of monohydric alkanol may range from 1 to 70%, preferably from 10 to 50%, optimally between 15 to 40% by weight.

Emollient materials may also serve as cosmetically acceptable carriers. These may be in the form of silicone oils and synthetic esters. Amounts of the emollients may range anywhere from 0.1 to 50%, preferably between 1 and 20% by weight.

Silicone oils may be divided into the volatile and non-volatile variety. The term "volatile" as used herein refers to those materials which have a measurable vapor pressure at ambient temperature. Volatile silicone oils are preferably chosen from cyclic or linear polydimethylsiloxanes containing from 3 to 9, preferably from 4 to 5, silicon atoms. Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 25 million centistokes at 25° C. Among the preferred non-volatile emollients useful in the present compositions are the polydimethyl siloxanes having viscosities from about 10 to about 400 centistokes at 25° C.

Among the ester emollients are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, myristyl myristate, stearyl stearate and arachidyl behenate.
(5) Sterols esters, of which cholesterol fatty acid esters are examples thereof.

Fatty acids having from 10 to 30 carbon atoms may also be included as cosmetically acceptable carriers for compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be employed as cosmetically acceptable carriers in compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The amount of humectant may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Amounts of the thickener may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight.

An oil or oily material may be present, together with an emulsifier to provide either a water-in-oil emulsion or an oil-in-water emulsion, depending largely on the average hydrophilic-lipophilic balance (HLB) of the emulsifier employed.

Surfactants may also be present in cosmetic compositions of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from 2 to 100 moles of ethylene oxide or propylene oxide per mole of hydrophobe; $C_2$–$C_{10}$ alkyl phenols condensed with from 2 to 20 moles of alkylene oxide; mono- and di-fatty acid esters of ethylene glycol; fatty acid monoglyceride; sorbitan, mono- and di-$C_8$–$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates, acyl glutamates, $C_8$–$C_{20}$ alkyl ether phosphates and combinations thereof.

Optional Components

In the cosmetic compositions of the invention, there may be added various medically effective ingredients, such as allantoin, a placenta extract; other thickeners, plasticizers; calamine; pigments; antioxidants; chelating agents; and perfumes; as well as additional sunscreens such organic sunscreens, typical of which are PARSOL 1789 and PARSOL MCX.

Other adjunct minor components may also be incorporated into the cosmetic compositions. These ingredients may include coloring agents, opacifiers, and perfumes. Amounts of these other adjunct minor components may range anywhere from 0.001% up to 20% by weight of the composition.

Sunscreens

For use as sunscreen, metal oxides may be used alone or in mixture and/or in combination with organic sunscreens. Examples of organic sunscreens include but are not limited those set forth in the table below:

TABLE 3

| CTFA Name | Trade Name | Supplier |
| --- | --- | --- |
| Benzophenone-3 | UVINUL M-40 | BASF Chemical Co. |
| Benzophenone-4 | UVINUL MS-40 | BASF Chemical Co. |
| Benzophenone-8 | SPECRA-SORB UV-24 | American Cyanamide |

TABLE 3-continued

| CTFA Name | Trade Name | Supplier |
|---|---|---|
| DEA | | |
| Methoxycinnamate | BERNEL HYDRO | Bernel Chemical |
| Ethyl dihydroxypropyl-PABA | AMERSCREEN P | Amerchol Corp. |
| Glyceryl PABA | NIPA G.M.P.A. | Nipa Labs. |
| Homosalate | KEMESTER HMS | Hunko Chemical |
| Methyl anthranilate | SUNAROME UVA | Felton Worldwide |
| Octocrylene | UVINUL N-539 | BASF Chemical Co. |
| Octyl dimethyl PABA | AMERSCOL | Amerchol Corp. |
| Octyl methoxycinnamate | PARSOL MCX | Bernel Chemical |
| Octyl salicylate | SUNAROME WMO | Felton Worldwide |
| PABA | PABA | National Starch |
| 2-Phenylbenzimidazole-5-sulphonic acid | EUSOLEX 232 | EM Industries |
| TEA salicylate | SUNAROME W | Felton Worldwide |
| 3-(4-methylbenzylidene)-camphor | EUSOLEX 6300 | EM Industries |
| Benzophenone-1 | UVINUL 400 | BASF Chemical Co. |
| Benzophenone-2 | UVINUL D-50 | BASF Chemical Co. |
| Benzophenone-6 | UVINUL D-49 | BASF Chemical Co. |
| Benzophenone-12 | UVINUL 408 | BASF Chemical Co. |
| 4-Isopropyl dibenzoyl methane | EUSOLEX 8020 | EM Industries |
| Butyl methoxy dibenzoyl methane | PARSOL 1789 | Givaudan Corp. |
| Etocrylene | UVINUL N-35 | BASF Chemical Co. |

The amount of the organic sunscreens in the cosmetic composition is preferably in the range of about 0.1 wt % to about 10 wt %, more preferably about 1 wt % to 5 wt %.

Preferred organic sunscreens are PARSOL MCX and Parsol 1789, due to their effectiveness and commercial availability.

Use of the Composition

The method according to the invention is intended primarily as using a personal care product for topical application to human skin, as well as to protect exposed skin from the harmful effects of excessive exposure to sunlight.

In use, a small quantity of the composition, for example from 1 to 5 ml, is applied to exposed areas of the skin, from a suitable container or applicator and, if necessary, it is then spread over and/or rubbed into the skin using the hand or fingers or a suitable device.

Product Form and Packaging

The cosmetic composition useful for the method of the invention can be formulated as a lotion having a viscosity of from 4,000 to 10,000 mPas, a fluid cream having a viscosity of from 10,000 to 20,000 mPas or a cream having a viscosity of from 20,000 to 100,000 mPas, or above. The composition can be packaged in a suitable container to suit its viscosity and intended use by the consumer. For example, a lotion or fluid cream can be packaged in a bottle or a roll-ball applicator or a propellant-driven aerosol device or a container fitted with a pump suitable for finger operation. When the composition is a cream, it can simply be stored in a non-deformable bottle or squeeze container, such as a tube or a lidded jar. When the composition is a solid or semi-solid stick, it may be packaged in a suitable container for manually or mechanically pushing out or extruding the composition.

The invention accordingly also provides a closed container containing a cosmetically acceptable composition as herein defined.

The following examples are by way of example, not by way of limitation, of the principles of the present invention, to illustrate the best mode of carrying out the invention.

EXAMPLE 1

The following compounds were used throughout the examples that follow. These compounds were prepared in accordance with the procedures set forth in this Example 1.

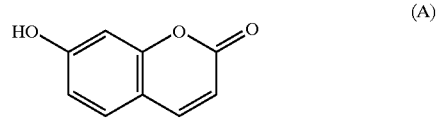

(A)

The compound of formula A, referred to herein as 7-hydroxy coumarin was used as a starting material to prepare the coumarin derived resorcinol compounds according to the present invention.

Synthesis of Resorcinol Amide 1

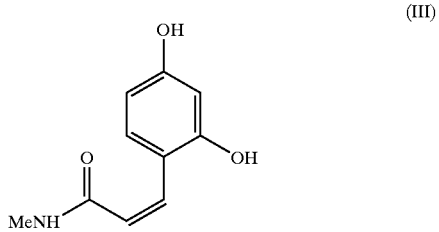

(III)

The compound of formula III is referred to herein Resorcinol Amide 1. To prepare resorcinol amide 1, 7-hydroxycoumarin (8.1 g; 0.05 mole; from Sigma-Aldrich, Milwaukee, Wis.) was dissolved in methanol (50 ml) and methyl amine was bubbled through the reaction. After 48 hrs, gas chromatography analysis showed the disappearance of 7-hydroxycoumarin. Methanol/methyl-amine was removed on a rotavap and the crude product was chromatographed on a silica column to give the resorcinol amide 1 in 75% isolated yield. The structure of this chemical was confirmed by Mass spectroscopy, NMR (H1 and C13) and Infrared.

Synthesis of Resorcinol Amide 2

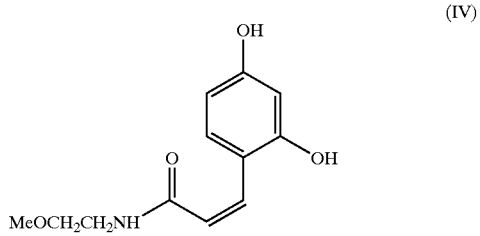

(IV)

The compound of formula IV is referred to herein as Resorcinol Amide 2. To prepare resorcinol amide 2, 7-hydroxycoumarin (16.2 g; 0.1 mole;) was dissolved in 2-methoxyethylamine (75.1 g; 1.0 mole, from Aldrich, Milwaukee, Wis.) and stirred at room temperature. After 24 hrs, gas chromatography analysis showed the disappearance of 7-hydroxycoumarin. The excess 2-methoxyethylamine was removed on a rotavap and the crude product was chromatographed on a silica column, to give the resorcinol amide 2 in 89% isolated yield. The structure of this chemical was confirmed by Mass spectroscopy, NMR (H1 and C13) and Infrared.

EXAMPLE 2

Cosmetic compositions within the scope of the invention were prepared.

A base formulation shown in Table 3, below, was made by heating phase A ingredients to 70 to 85° C. with stirring. Phase B ingredients were heated in a separate container to 70 to 85° C. with stirring. Then, phase A was added into phase B while both phases were kept at 70 to 85° C. The mixture was stirred for at least 15 minutes at 70 to 85° C., then cooled.

A base formulation is shown in the table below.

TABLE 4

| Ingredients | 3a % wt. | 3b % wt. | Phase |
|---|---|---|---|
| Isostearyl Palmitate | 6.00 | 6.00 | A |
| C12–C15 Alkyl Octanoate | 3.00 | 3.00 | A |
| PEG-100 Stearate | 2.00 | 2.00 | A |
| Glyceryl Hydroxystearate | 1.50 | 1.50 | A |
| Stearyl Alcohol | 1.50 | 1.50 | A |
| Stearic acid | 3.00 | 4.00 | A |
| TEA, 99% | 1.20 | 1.20 | B |
| Dimethicone | 1.00 | 1.00 | A |
| Sorbitan Monostearate | 1.00 | 1.00 | A |
| Magnesium Aluminum Silicate | 0.60 | 0.60 | B |
| Vitamin E acetate | 0.10 | 0.10 | A |
| Cholesterol | 0.50 | 0.50 | A |
| Simethicone | 0.01 | 0.01 | B |
| Xanthan gum | 0.20 | 0.20 | B |
| Hydroxyethylcellulose | 0.50 | 0.50 | B |
| Propylparaben | 0.10 | 0.10 | B |
| Disodium EDTA | 0.05 | 0.05 | B |
| Butylated hydroxytolene | 0.05 | 0.05 | B |
| Resorcinol Amide 1 | 0.05 | 2.00 | B |
| Niacinamide | 1.00 | 1.00 | B |
| Metal oxide | 2.50 | 5.00 | B |
| Methylparaben | 0.15 | 0.15 | B |
| Water | BAL* | BAL* | B |
| Total | 100.00 | 100.00 | B |

*BAL means Balance.

EXAMPLE 3

Additional cosmetic compositions within the scope of the invention were prepared.

TABLE 5

| | Wt % | Phase |
|---|---|---|
| water, DI | BALANCE | A |
| disodium EDTA | 0.05 | A |
| magnesium aluminum silicate | 0.6 | A |
| methyl paraben | 0.15 | A |
| simethicone | 0.01 | A |
| butylene glycol 1,3 | 3.0 | A |
| hydroxyethylcellulose | 0.5 | A |
| glycerine, USP | 2.0 | A |
| xanthan gum | 0.2 | A |
| triethanolamine | 1.2 | B |
| stearic acid | 3.0 | B |
| propyl paraben NF | 0.1 | B |
| glyceryl hydroxystearate | 1.5 | B |
| stearyl alcohol | 1.5 | B |
| isostearyl palmitate | 6.0 | B |
| C12–15 alcohols octanoate | 3.0 | B |
| dimethicone | 1.0 | B |
| cholesterol NF | 0.5 | B |
| sorbitan stearate | 1.0 | B |
| Micronized titanium dioxide | 5.0 | C |
| tocopheryl acetate | 0.1 | B |
| PEG-100 stearate | 2.0 | B |
| sodium stearoyl lactylate | 0.5 | B |
| hydroxycaprylic acid | 0.1 | C |
| Resorcinol Amide 2 | 10.0 | C |
| PARSOL MCX | 2.4 | C |
| alpha-bisabolol | 0.2 | C |

The composition of Example 3, was prepared as follows:

1. Heat Phase A to 80° C.
2. Heat Phase B to 75° C. in a separate container
3. Add B to A and mix with heat off for 30 min.
4. At 50° C. add Phase C and mix for 10 min.

EXAMPLES 4–11

A set of additional compositions useful in the methods of the present invention were prepared within the scope of the present invention and are listed in the table below.

TABLE 6

| | | Examples (wt. %) | | | | | | | |
|---|---|---|---|---|---|---|---|---|---|
| Ingredients | Phase | 3 acid soap base | 4 | 5 | 6 | 7 | 8 | 9 | 10 |
| Stearic acid | A | 17.9 | 17.9 | 17.9 | 17.9 | 17.9 | 17.9 | 17.9 | 17.9 |
| Sodium cetearyl sulfate* (emulsifier) | A | | 2.2 | | 1 | 1.5 | 2 | 3 | 2 |
| Myrj 59* (emulsifier) | A | | | 2 | 2 | 2 | 2 | 2 | 1 |
| Span 60* (emulsifiers) | A | | | 2 | 2 | 2 | 2 | 2 | 1 |
| Resorcinol Amide 1 | B | 0.05 | 0.05 | 2.0 | 2.0 | 3.5 | 3.5 | 5.0 | 10.0 |
| Micronized Zinc Oxide | B | 2.50 | 5.00 | 5.00 | 2.50 | 2.50 | 5.00 | 2.50 | 5.00 |
| KOH, 22% (form in situ soap with stearic acid) | | 2.20 | | | | | | | |
| Octyl methoxycinnamate | | | 2.50 | | 2.50 | 2.50 | | 2.50 | |
| Water | B | | BAL | BAL | BAL | BAL | BAL | BAL | BAL |
| Glycerin | B | 1 | 1 | 1 | 1 | 1 | 1 | 1 | 1 |

EXAMPLE 12

This example shows the skin lightening effect of using 7-hydroxy-coumarin derived resorcinol compounds as skin lightening agents in accordance with the inventive method. This experiment was carried out using a cell based assay.

B16 mouse melanoma cells were utilized in the following experiment to evaluate the efficacy of skin lightening agents. B16 cells were plated in 96-well microtiter plates at a density of 5000 cells per well and cultured overnight in Dulbecco's Modified Eagle's Medium (phenol red free) containing 10% fetal bovine serum and 1% penicillin/streptomycin at 37° C. in the presence of 5% $CO_2$. After 24 hours, the medium was replaced with fresh growth medium containing the treatments. All cultures were incubated for 72 hours at which time melanin was visible in the control treatment. The melanin-containing medium was transferred to a clean 96-well plate and quantified by reading the absorbency at 530-nm. Cell viability was assessed by measurement of lactate dehydrogenase levels to ensure the decrease in melanin was not a result of cellular toxicity.

TABLE 7

| Compound | Concentration | % of Control (Melanin Synthesis) |
| --- | --- | --- |
| 4-Ethyl Resorcinol | 6.25 micromolar | 15.6% |
| Resorcinol Amide 1 | 6.25 micromolar | 13.1% |
| Resorcinol Amide 2 | 6.25 micromolar | 13.7% |

From the results tabulated above it appears that coumarin derived resorcinol compounds of the present invention reduce melanin synthesis to about the same or better degree than 4-ethyl resorcinol.

EXAMPLE 13

Mushroom Tyrosinase Assay

Mushroom tyrosinase inhibition is indicative of reduction in melanin synthesis, thereby showing skin lightening effect. This experiment shows the efficacy of coumarin derived resorcinol derivatives of the present invention.

Into each well of a 96-well plate, 150 microliters of phosphate buffer (100 mM, pH 7.0), 10 microliters of L-DOPA (L-3, 4-Dihydroxyphenylalanine, 10 mM), and 20 microliters of skin lightening agent (dissolved in ethanol, which is the control) were added. Following an initial measurement of background absorbency at 475-nm, 20 microliters of mushroom tyrosinase (Sigma T-7755; 6050 units/ml) was added and incubated at room temperature.

Absorbency is read at 475-nm over the following time points: 0, 2, 4, and 6.5 minutes. The data is plotted as 475-nm absorbency vs. time (minutes) and the slope of the line is calculated ($\Delta$Abs 475 nm/min). Values are expressed as the percentage of the respective untreated ethanol control reaction.

$$\% \text{ of Control} = \frac{\text{(Reaction rate for treated reaction)}}{\text{(Reaction rate for untreated control)}} \times 100\%$$

TABLE 8

| Compound | Concentration | % of Control (Melanin Synthesis) |
| --- | --- | --- |
| 4-Ethyl Resorcinol | 0.1 uM | 72.7 |
| | 1 uM | 46.3 |
| | 10 uM | 30.8 |
| | 100 uM | 20.7 |
| 7-Hydroxy Coumarin | 0.1 uM | 104 |
| | 1 uM | 100 |
| | 10 uM | 108 |
| | 100 uM | 117 |
| Resorcinol Amide 1 | 0.1 uM | 75.1 |
| | 1 uM | 51.0 |
| | 10 uM | 53.0 |
| | 100 uM | 53.4 |
| Resorcinol Amide 2 | 0.1 uM | 84.2 |
| | 1 uM | 59.5 |
| | 10 uM | 58.0 |
| | 100 uM | 57.9 |

The data show that the hydrolyzed coumarin amide is substantially as effective as 4-ethyl resorcinol, both compounds having good skin lightening effects. The 7-hydroxy coumarin compound from which the compounds of the present invention may be derived is effective in skin lightening.

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic method of skin lightening comprising applying to the skin a composition comprising:
   a. about 0.000001 to about 50% of a compound of general formula I

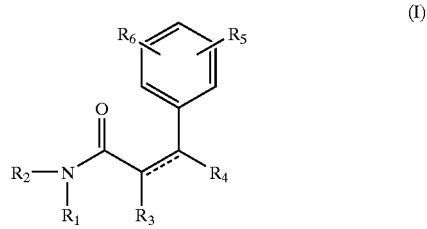

(I)

Wherein each or both $R_1$ and/or $R_2$ is selected from the group consisting of hydrogen; linear or branched $C_1$–$C_{18}$ alkyl, alkenyl, cycloalkyl, cycloalkenyl, hydroxyalkyl; hydroxyalkenyl, acyl; cycloacyl, and alkoxy groups;

Wherein each or both $R_3$ and/or $R_4$ is selected from the group consisting of hydrogen; linear or branched $C_1$–$C_{18}$ alkyl, alkenyl, alkoxy, cycloalkyl, and cycloalkenyl group; wherein the dotted line is a single or double carbon-carbon bond;

Wherein each or both $R_5$ and/or $R_6$ is selected from the group consisting of a hydrogen atom, OH, $C_1$–$C_4$ acyl group, $C_1$–$C_4$ alkyl group, O—CO—$R_7$, or O—COO—$R_8$ group; wherein each or both $R_7$ and/or $R_8$ is selected from the group consisting of hydrogen; linear or branched $C_1$–$C_{18}$ alkyl, alkenyl, hydroxyalkyl, hydroxyalkenyl, acyl, cycloacyl, or alkoxy groups;

wherein R₅ and/or R₆ may be positioned at the 1-, 2-, 3-, 5-, and/or 6-positions on the phenyl ring; and b. a cosmetically acceptable carrier.

2. The method of claim 1, wherein said composition further comprises a sunscreen.

3. The method of claim 2, wherein said sunscreen is a micronized metal oxide.

4. The method of claim 1, wherein said compound is a hydroxy coumarin derived resorcinol derivative.

5. The method of claim 1, wherein said compound is a compound of general formula II:

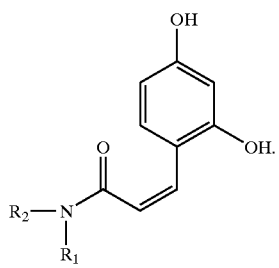

(II)

6. The cosmetic method of claim 1, wherein R₁ and R₂ both represent hydrogen.

7. The cosmetic method according to claim 1, wherein said composition further comprises a skin benefit agent selected from the group consisting of alpha-hydroxy acids, beta-hydroxy acids, polyhydroxy acids, hydroquinone, t-butyl hydroquinone, Vitamin C derivatives, dioic acids, retinoids, resorcinol derivatives, and mixtures thereof.

8. The cosmetic method of claim 1, wherein said composition further comprises an organic sunscreen selected from the group consisting of Benzophenone-3, Benzophenone-4, Benzophenone-8, DEA, Methoxycinnamate, Ethyl dihydroxypropyl-PABA, Glyceryl PABA, Homosalate, Methyl anthranilate, Octocrylene, Octyl dimethyl PABA, Octyl methoxycinnamate (PARSOL MCX), Octyl salicylate, PABA, 2-Phenylbenzimidazole-5-sulphonic acid, TEA salicylate, 3-(4-methylbenzylidene)-camphor, Benzophenone-1, Benzophenone-2, Benzophenone-6, Benzophenone-12, 4-Isopropyl dibenzoyl methane, Butyl methoxy dibenzoyl methane (PARSOL 1789), Etocrylene, and mixtures thereof.

9. A cosmetic composition comprising:
 a. about 0.000001 to about 50% of a compound of general formula I

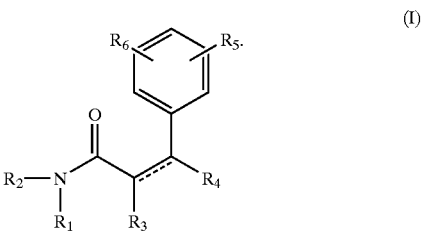

(I)

wherein each or both R₁ and/or R₂ is selected from the group consisting of hydrogen; linear or branched C₁–C₁₈ alkyl, alkenyl, cycloalkyl, cycloalkenyl, hydroxyalkyl; hydroxyalkenyl, acyl; cycloacyl, and alkoxy groups;

wherein each or both R₃ and/or R₄, is selected from the group consisting of hydrogen; linear or branched C₁–C₁₈ alkyl, alkenyl, alkoxy, cycloalkyl, and cycloalkenyl group; wherein the dotted line is a single or double carbon-carbon bond;

wherein each or both R₅ and/or R₆ is selected from the group consisting of a hydrogen atom, OH, C₁–C₄ acyl group, C₁–C₄ alkyl group, O—CO—R₇, or O—COO—R₈ group, wherein each or both R₇ and/or R₈ is selected from the group consisting of hydrogen; linear or branched C₁–C₁₈ alkyl, alkenyl, hydroxyalkyl, hydroxyalkenyl, acyl, cycloacyl, or alkoxy groups;

Wherein R₅ and/or R₆ may be positioned at the 1-, 2-, 3-, 5-, and/or 6-positions on the phenyl ring; and b. a cosmetically acceptable carrier.

10. The cosmetic composition of claim 9, wherein said compound is a compound of general formula II:

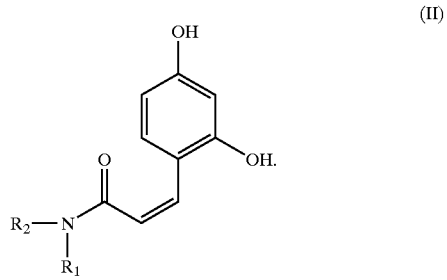

(II)

11. The cosmetic composition of claim 10, wherein R₁ and R₂ both represent hydrogen.

12. The cosmetic composition of claim 9, wherein said compound comprises about 0.00001% to about 10% of said composition.

13. The cosmetic composition of claim 9, wherein said compound comprises about 0.001% to about 7% of said composition.

14. The cosmetic composition of claim 9, wherein said compound comprises about 0.01% to about 5% of said composition.

* * * * *